US006656188B2

(12) United States Patent
Naybour et al.

(10) Patent No.: US 6,656,188 B2
(45) Date of Patent: Dec. 2, 2003

(54) TAMP ASSEMBLY

(75) Inventors: John Naybour, Mold (GB); David Moore, Leicester (GB)

(73) Assignee: Depuy Products, Inc., Warsaw, IN (US)

( * ) Notice: Subject to any disclaimer, the term of this patent is extended or adjusted under 35 U.S.C. 154(b) by 0 days.

(21) Appl. No.: 09/989,067

(22) Filed: Nov. 21, 2001

(65) Prior Publication Data

US 2002/0065518 A1 May 30, 2002

(30) Foreign Application Priority Data

Nov. 22, 2000 (GB) .......................................... 00288445

(51) Int. Cl.$^7$ ................................................ A61F 5/00
(52) U.S. Cl. ....................................................... 606/86
(58) Field of Search .............................. 606/62, 86, 92, 606/94, 93, 105; 623/908, 23.48

(56) References Cited

U.S. PATENT DOCUMENTS

| 5,843,086 | A | * | 12/1998 | Huyser et al. ................ 606/92 |
| 5,899,907 | A | * | 5/1999 | Johnson ........................ 606/73 |
| 5,910,172 | A | * | 6/1999 | Penenberg ................... 623/23 |
| 5,925,051 | A | | 7/1999 | Mikhail |
| 6,022,355 | A | * | 2/2000 | Peche et al. .................. 606/93 |
| 6,217,583 | B1 | * | 4/2001 | Storer .......................... 606/92 |
| 6,228,091 | B1 | * | 5/2001 | Lombardo et al. ............ 606/88 |
| 6,228,092 | B1 | * | 5/2001 | Mikhail ....................... 606/105 |
| 6,270,502 | B1 | * | 8/2001 | Stulberg ....................... 606/86 |

FOREIGN PATENT DOCUMENTS

| EP | 555004 A | 8/1993 |
| EP | 780092 A | 6/1997 |
| EP | 888752 A | 1/1999 |
| EP | 992 225 A2 | 12/2000 |

* cited by examiner

*Primary Examiner*—Eduardo C. Robert
(74) *Attorney, Agent, or Firm*—John S. Wagley

(57) ABSTRACT

A tamp assembly for use in configuring bone cavity filler material within a bone cavity, in preparation for receiving an implant, includes a distal tamp portion which has a substantially constant cross-section over at least part of its length. A proximal tamp portion has a through bore extending through it with a size which is such that the proximal tamp portion is a sliding fit over the distal tamp portion. The proximal tamp portion has an exterior tamping surface extending from the through bore which faces generally towards the distal tamp portion. The assembly includes a hammer for transmitting impact to the bone cavity filler material which is contacted by the tamping surface of the proximal tamp portion.

12 Claims, 5 Drawing Sheets

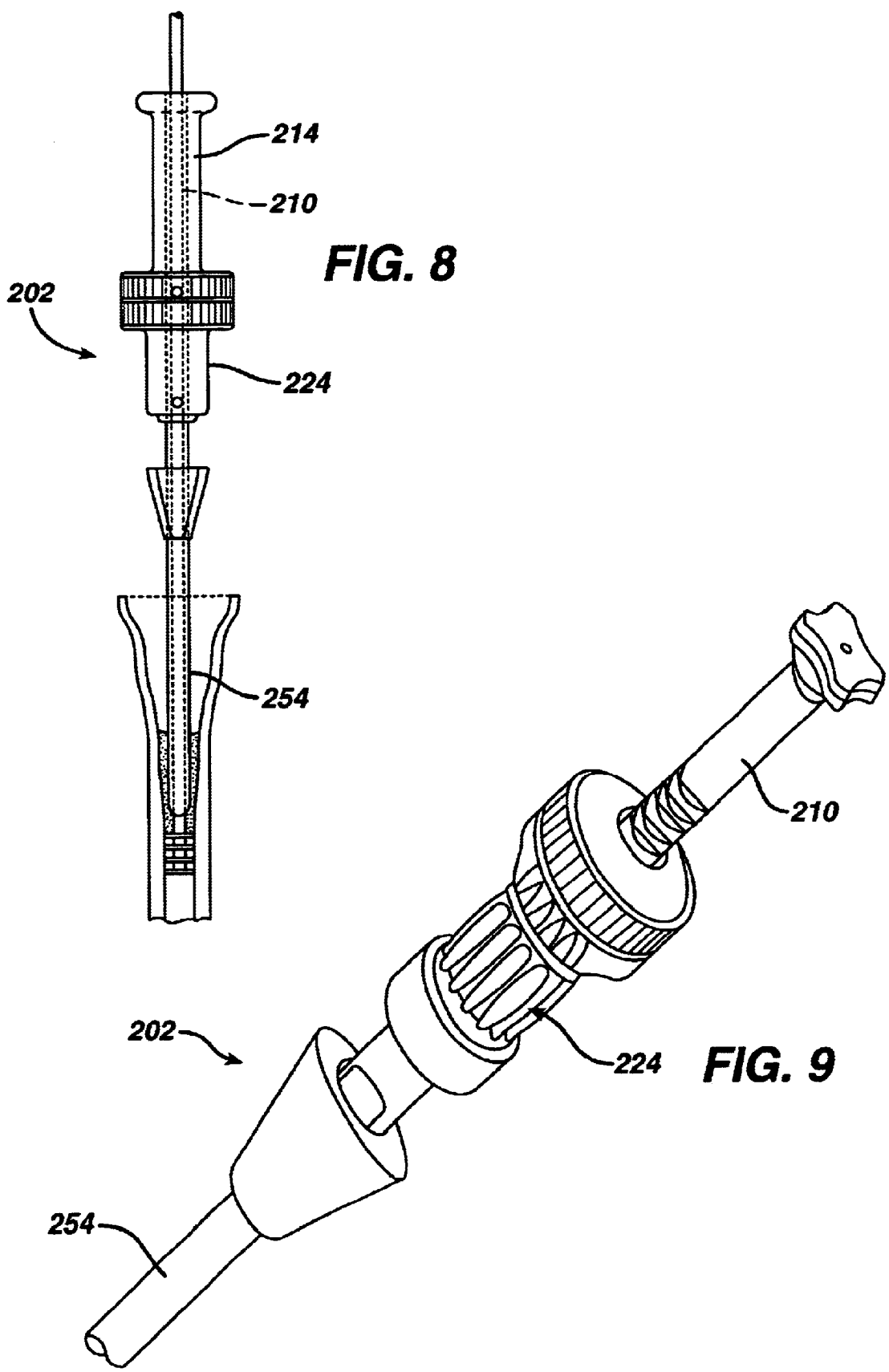

TAMP ASSEMBLY

BACKGROUND TO THE INVENTION

This invention relates to a tamp assembly for use in configuring bone cavity filler material within a bone cavity, in preparation for receiving an implant.

It can be necessary to prepare a bone cavity to receive an implant during replacement of a bone joint. For example, the cavity within a femur has to be prepared to receive the femoral component of a hip joint prosthesis and cavities within the femur and tibia have to be prepared to receive respective components of a knee joint prosthesis.

Joint prosthesis components can be fixed within a bone cavity by means of bone cement materials. They can also be fixed within a bone cavity by relying on the natural bone tissue, especially by providing the components with an appropriate surface finish which promotes bone ingrowth.

It can be important to configure the cavity so that the prosthesis component fits into it with minimum space left empty within the cavity around the component. For this purpose, the cavity is generally prepared by providing a filler material within it. The filler material is compatible with the prosthesis component and the technique by which it is to be fixed in place. It should also be conformable so that it can be shaped to configure the cavity appropriately for the selected component. For example, when the component is to be fixed within the cavity by means of a bone cement, the filler material will be a bone cement. When the component is to be fixed within the cavity relying on natural bone tissue, the filler material can be a bone graft material.

Filler material that is located in the bone cavity needs to be packed densely within the cavity to minimise voids. It also needs to be shaped to match the configuration of the prosthesis. It is known (for example from WO-A-93/1773) to shape bone graft material within a bone cavity by means of a tamp which is forced into the cavity to compress the material so that it adopts the configuration that is desired to suit the prosthesis that is to be implanted. A surgeon might use a number of tamps in sequence, whose configurations tend closer to that of the prosthesis. The tamps slide over a guide wire which is fitted in the cavity in a bone plug. The guide wire defines the path for the tamp to move along when it is being used to compress the bone graft material. When the tamping operation is complete, the guide wire is removed, leaving a cavity whose shape is defined by the shape of the tamps. This technique has been found to be an advantageous technique for making the filler material dense and also match the configuration of the prosthesis component to be implanted. For example, the configuration of a set of tamps for a prosthesis that is tapered gradually towards its tip might change from being tapered sharply so that it is wide at its end facing the handle, to being tapered less sharply so that it is relatively narrow at its end facing the handle.

A disadvantage of using a plurality of separate tamps can arise when a tamp has to be removed from within the bone cavity to be replaced by another tamp. Removal of the tamp can result in the filler material within the cavity being loosened or otherwise disturbed.

SUMMARY OF THE INVENTION

The present invention provides a tamp assembly for use in configuring bone cavity filler material within a bone cavity, in preparation for receiving an implant, which comprises:

1. a distal tamp portion which has a substantially constant cross-section over at least part of its length,
2. a proximal tamp portion which has a through bore extending through it with a size which is such that the proximal tamp portion is a sliding fit over the distal tamp portion, and which has an tamping surface extending from the through bore which faces generally towards the distal tamp portion, and
3. a hammer for transmitting impact to the bone cavity filler material which is contacted by the tamping surface of the proximal tamp portion.

The assembly of the invention has the advantage that the configuration of the tamp (which is made up of the distal and proximal tamp portions together) can be changed by replacing one proximal tamp portion with another which has a different shape. The distal tamp portion which defines the shape of the cavity at the distal end thereof can therefore remain in place throughout the tamping operation, which means that the filler material within the cavity at is distal end is not disturbed by unnecessary movement of the distal tamp portion.

The references to components of the assembly as "distal" and "proximal" should be understood as being relative to the resection of the bone which is to receive the implant and not in accordance with conventional anatomical uses of these terms. Accordingly, the distal tamp component is located further from the bone resection than the proximal tamp component.

Preferably, the assembly includes a guide shaft which is aligned with the distal tamp portion. The hammer can then have a through bore extending through it with a size which is such that it is a sliding fit over the guide shaft. This enables the impact that is imparted to the filler material through the proximal tamp portion (and often also the distal tamp portion) to be properly directed.

The hammer can be arranged so that it is moved to contact the proximal tamp portion which is stationary, in contact with the bone cavity filler material, to transmit impact to the filler material. In a different arrangement, the proximal tamp portion and the hammer can have mating formations which enable them to be fastened to one another so that they are moved together to contact the bone cavity filler material in order to transmit impact to it. For example, the formations might take the form of threads, or a spring loaded catch or the like; the fastening which is provided by the formations should be such that it does not become loose when the hammer and the proximal tamp portion are moved to impact the bone cavity filler material.

The configuration of the distal tamp portion will often be generally cylindrical (which can involve a slight inward taper towards the distal end to ease withdrawal of the tamp after use). When the distal tamp portion has a cross-section which changes significantly along its length, it can be preferred for the assembly to include more than one distal tamp portion, for example which differ by the cross-section and its variation along the length of the tamp portion. Different distal tamp portions within an assembly can have different cross-sectional configurations. Generally, they will be generally rounded, especially circular. The distal tamp portion that is selected for a particular patient will depend on the transverse dimensions of the cavity within the bone, which often will have been reamed so a predetermined diameter using known reaming techniques. In this case, the distal tamp portion will be selected so that its transverse dimensions are consistent with those of the reamer and of course of the implant that is to be used. The diameter of the distal tamp portion will generally be at least about 5 mm, preferably at least about 7 mm, more preferably at least about 10 mm. For some patients, the diameter of the distal tamp portion will be at least 12 mm, or even up to 15 mm or more.

The configuration of the proximal tamp portion will be selected according to the shape of the cavity within the bone in which the filler material is to be compressed, and to the shape of the implant which is to be fitted within the filled cavity. When the volume within the cavity which is to be filled with filler material is large so that the layer of the filler material is thick (at least in a part of the cavity), it can be preferred for progressively smaller tamp portions to be used so that the filler material is compressed within the bone cavity in layers. The assembly can include a proximal tamp portion whose tamping surface is tapered outwardly from its distal end towards its proximal end. It can include a proximal tamp portion with a tamping surface facing towards the distal tamp portion which is generally planar.

Accordingly, it can be preferred for the assembly of the invention to include a plurality of proximal tamp portions of different configurations. A group of the proximal tamp portions can have through bores which are substantially the same size so that all of the proximal tamp portions are a sliding fit over a common distal tamp portion, the proximal tamp portions being tapered outwardly from the distal ends thereof towards their proximal ends, and differing in the configuration of the outward taper. It can also be preferred for the assembly to include at least one proximal tamp portion whose tamping surface which faces towards the distal tamp portion is generally planar. Generally, a tamp portion with a planar tamping surface is used to finish the top surface of the filler material at the point at which the bone is resected. Such a tamp portion can be used as a cavity-end tamp portion, having a through bore extending through it whose size which is such that the cavity-end tamp portion is a sliding fit over the distal tamp portion, and which has a mould surface facing into the bone cavity when the cavity-end tamp portion is in use, to shape the bone cavity filler material to receive an implant at the exposed end of the cavity.

When the assembly includes a guide shaft for the hammer, it can be formed as a separate part from the distal tamp portion so that it can be fixed to the distal tamp portion. For many applications, it will be preferred however for the guide shaft and the distal tamp portion to be formed as a single component. The guide shaft and the distal tamp portion can have the same external cross-section so that they provide a continuous surface for the hammer to move over during the tamping action. When the through bore in the hammer is bigger than the cross-section of the guide shaft so that it is a loose fit thereon, the assembly can include an adaptor sleeve which fits over the guide shaft and within the through bore within the hammer, to provide a sliding fit between the guide shaft and the hammer.

Preferably, the assembly includes includes a cap on the guide shaft with a impact surface facing along the guide shaft towards the proximal tamp portion, onto which impact can be directed to loosen the assembly from within the bone cavity. It is preferred that the cap is arranged so that the impact surface is so that it is engaged by the hammer as it is slid over the guide shaft.

A suitable cap can be fastened to the guide shaft (directly or indirectly) by means of appropriate formations such as screw threads, bayonet formations and the like.

Materials which can be used to make the tamp assembly include metals and plastics. Examples include certain steels, aluminium and titanium alloys, and epoxy and polyester resins, especially when reinforced with fibres such as carbon fibres. Generally, metal materials will be used because of their ability to withstand impact.

Filler materials which can be tamped using the assembly of the invention include materials which encourages the growth of natural bone tissue by which the prosthesis can be secured in place within the cavity; suitable materials include morcellised bone graft. The filler material might be a cement material which itself forms a bond to the prosthesis; commonly used bone cement materials include those based on acrylate materials.

A bone plug can be placed within the bone cavity to control the distribution of the filler material within the cavity and to prevent unwanted movement of the filler material away from the resected end of the bone. The bone plug can provide a fixing point for a guide rod. The distal tamp portion, generally together with the guide shaft, can be cannulated so that they can slide over the guide rod which to control the orientation of the distal tamp portion and other components whose orientations are controlled by it. Such use of a guide rod is generally as disclosed in WO-A-93/1773.

INTRODUCTION TO THE DRAWINGS

FIG. 8 is a side elevation, partially in section, through the assembly of yet another embodiment of the present invention showing the guide shaft and the distal tamp portion as separate components.

FIG. 9 is an isometric view of the hammer, proximal tamp portion and the proximal end of the distal tamp portion and the guide shaft of the tamp assembly shown in FIG. 8.

DESCRIPTION OF PREFERRED EMBODIMENTS

Figure 1:
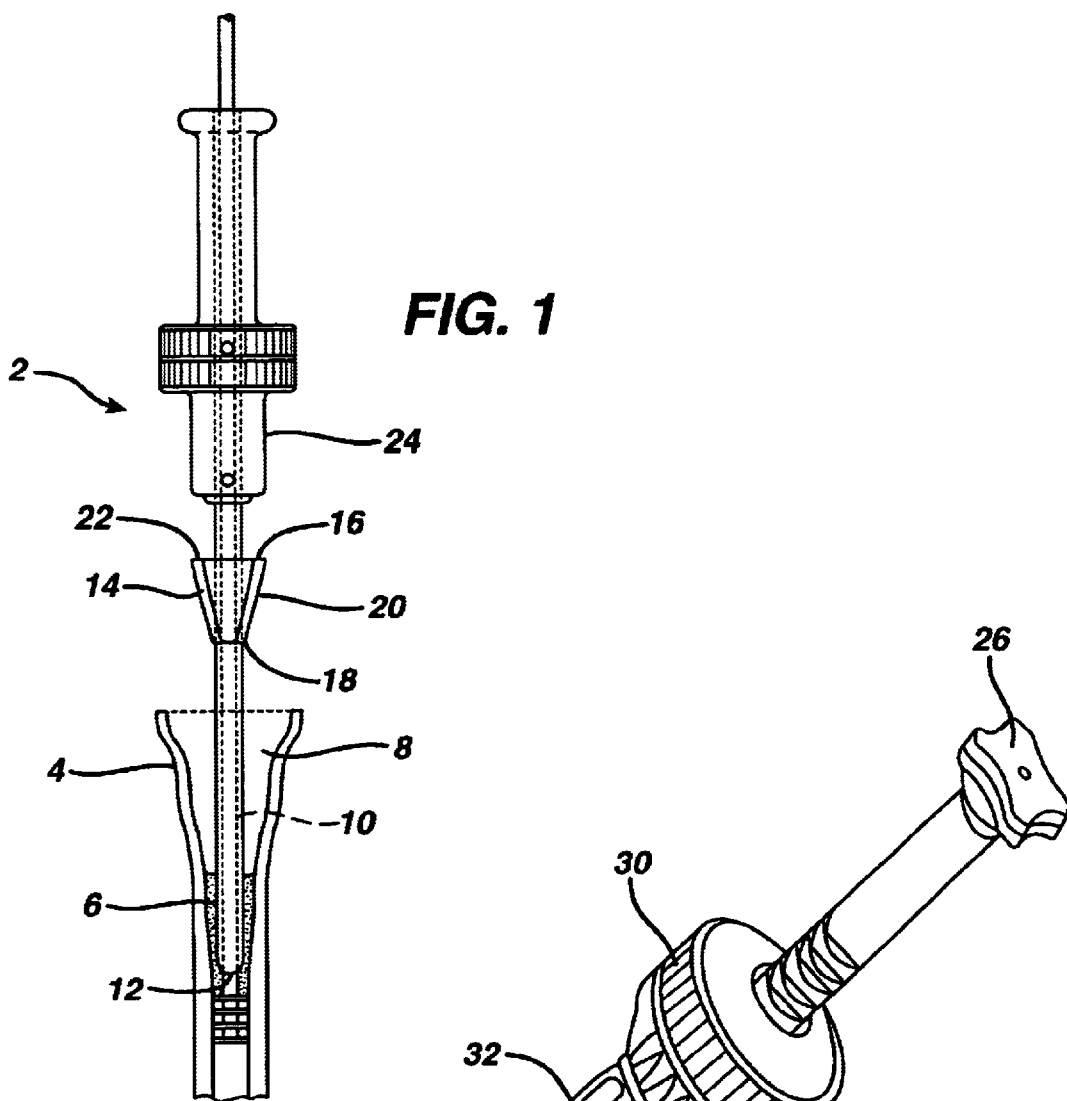
FIG. 1 is a side elevation, partially in section, through the assembly of the invention in use.

FIG. 1 shows a tamp assembly 2 positioned relative to a resected tibia 4 so as to tamp morcellised bone graft material 6 into the cavity 8 within the tibia, to receive the tibial component of a prosthetic knee joint.

The assembly includes a distal tamp portion 10 which has a substantially constant circular cross-section with a diameter which corresponds approximately to the internal dimensions of the bone cavity. For a typical patient, the tamp diameter will be about 10 mm. The distal tamp portion extends continuously over a length of about 40 cm and has a substantially constant cross-section over that length. The end 12 of the distal tamp portion is rounded.

A proximal tamp portion 14 has a through bore 16 extending through it, so that it can receive the distal tamp portion 10 to extend through it. The proximal tamp portion has an external cross-section at its distal end 18 which is approximately the same as the external cross-section of the distal tamp portion. It has an external surface 20 which flares outwardly towards its proximal end 22.

The proximal tamp portion 14 is connected to a hammer 24 which also has a through bore extending through it, so that it too can receive the distal tamp portion 10 to extend through it. Both the proximal tamp portion and the hammer can be slid along the distal tamp portion.

Figure 2:
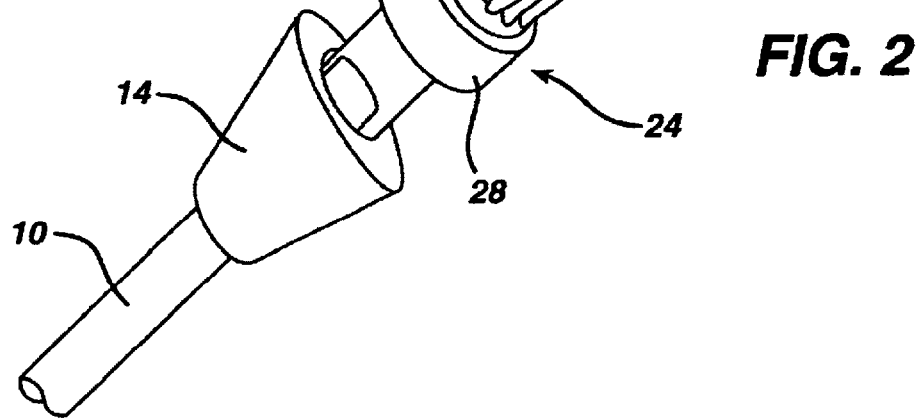
FIG. 2 is an isometric view of the hammer, proximal tamp portion and the proximal end of the distal tamp portion (which provides the guide shaft) of the tamp assembly shown in FIG. 1.

FIG. 2 shows the assembly of the proximal tamp portion 14 and the hammer 24, positioned on the distal tamp portion (or guide shaft) 10. They are connected to one another by a releasible connection mechanism which allows them to be separated from one another. This allows different proximal tamp portions to be used during the course of a surgical procedure, to tamp layers of filler material successively in order to fill a bone cavity.

The assembly includes a cap 26 which is threadably attached to the guide shaft at its top end. The cap 26 has to be removed from the guide shaft in order to allow the hammer and the proximal tamp portion to be removed from the guide shaft.

The hammer 24 has a pair of circumferential flanges 28, 30 and a portion 32 between them with axially extending ridges, which enable the hammer to be gripped conveniently by a user.

Figure 3:
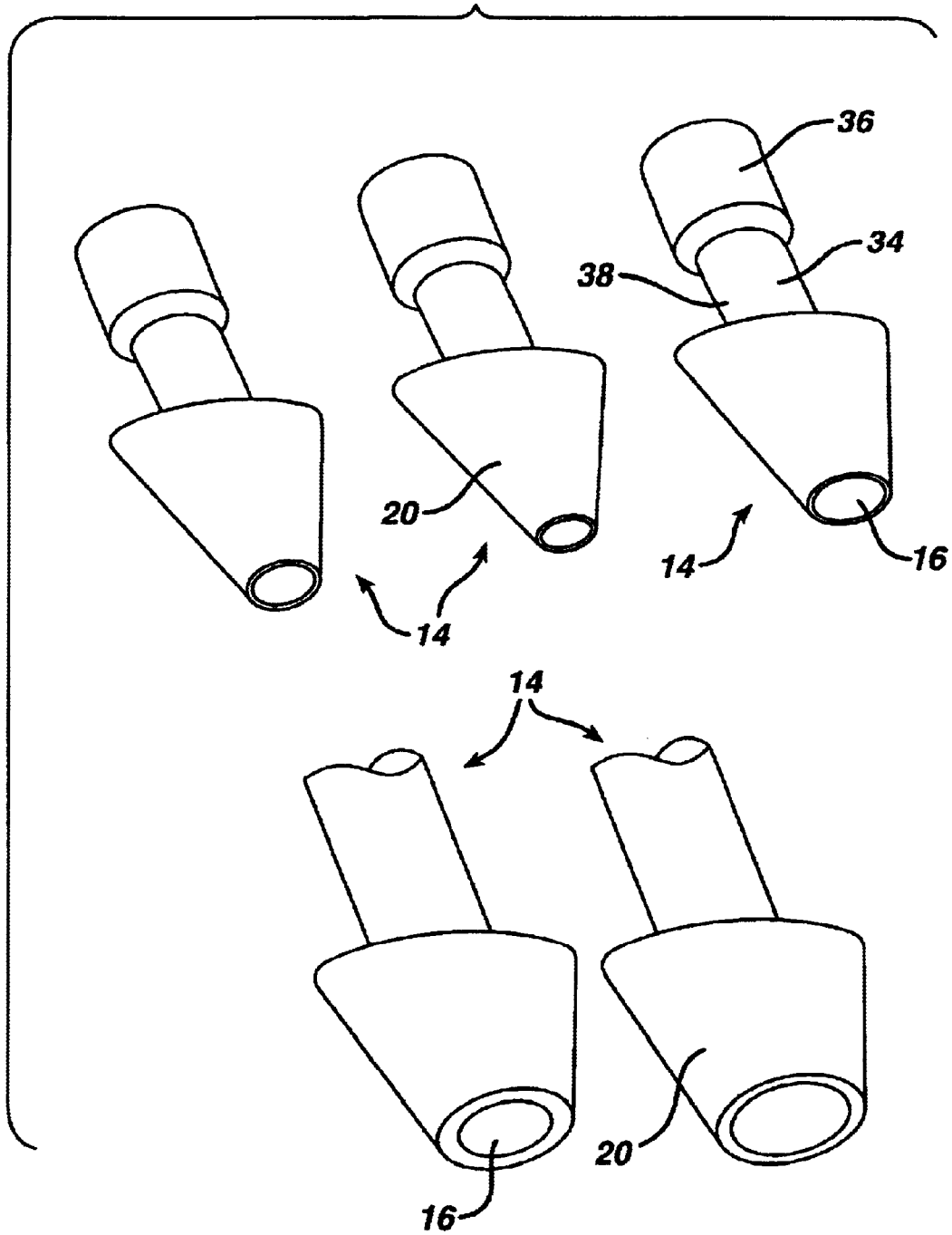
FIG. 3 is an isometric view of a plurality of proximal tamp portions.

FIG. 3 shows a plurality of proximal tamp portions 14 which can be used in the assembly of the invention. They differ from one another by having through bores 16 with different internal diameters, and by having differently shaped tamping surfaces 20. Each of the tamp portions includes a shaft 34 which terminates in a collar 36 at its upper end, which is received within the hammer. A groove 38 which extends between the tamping surface 20 and the collar 36 can be gripped by the hammer when the two are connected to one another.

The height of the proximal tamp portions (measured along the axis of the through bore) will be arranged so that they can compress filler material to the desired depth within the bone cavity. Proximal tamp portions for one application (for example for the tibial component of a knee joint prosthesis) might be different from proximal tamp portions for another application (for example the femoral component of a hip prosthesis). In the case of the tibial component of a knee joint prosthesis, the height of the proximal tamp portions might be about 4 cm.

Figure 4:
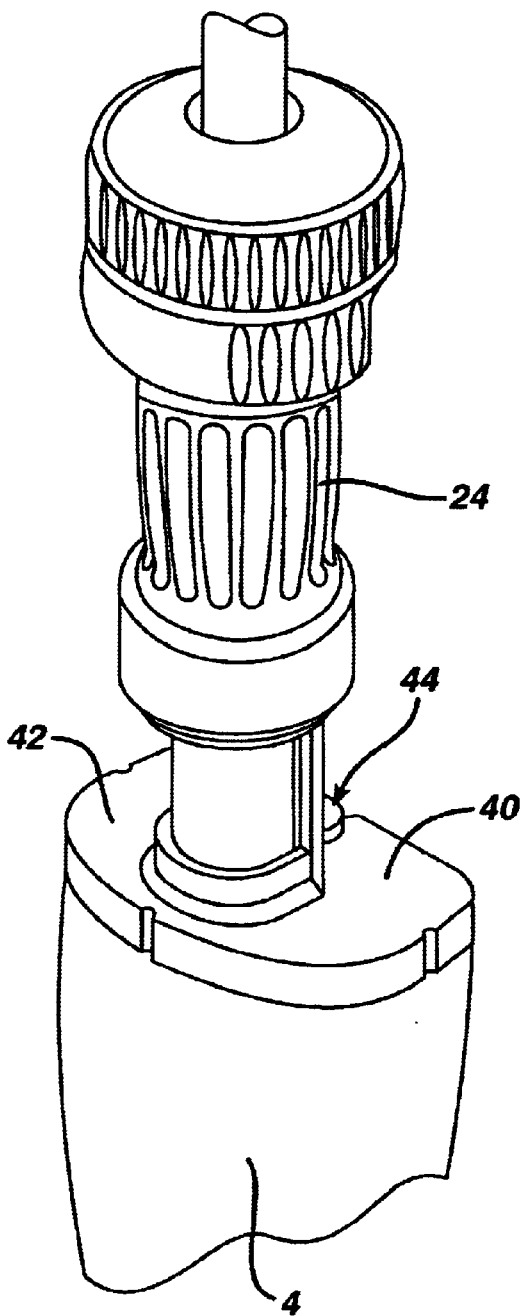
FIG. 4 is an isometric view of the assembly of the invention, in use to finish the surface of the filler material in a bone cavity using a cavity-end tamp portion.

FIG. 4 shows a patient's tibia 4 in which the bone cavity 8 has been filled with filler material 6. The assembly 2 can be used to finish the upper surface of the bone assembly, using a cavity-end tamp portion 40. The cavity-end tamp portion has a planar tamping surface 42. A through bore 44 extends through the tamp portion, and is sized so that the tamp portion is a sliding fit over the guide shaft 10. The cavity-end tamp portion is connected to the hammer 24 so that the connected components can be slid on the guide shaft in a manner similar to the connected hammer and proximal tamp portion.

Figure 5:
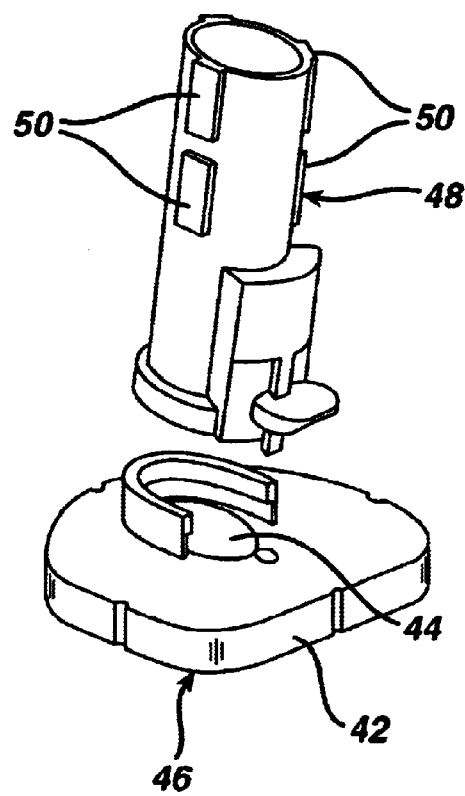
FIG. 5 is an isometric view of a proximal tamp portion which can provide a cavity-end tamp portion as shown in FIG. 4, with an adaptor by which it can be fastened to a hammer.

FIG. 5 is an enlarged view of a cavity-end tamp portion 40 in two parts. A first part 46 has the tamping surface 42 on its underside and the through bore 44 extending through it.

A second adaptor part 48 can be connected rigidly to the first part and has formations 50 on it which enable it to be connected rigidly to the hammer 24.

Figure 6:
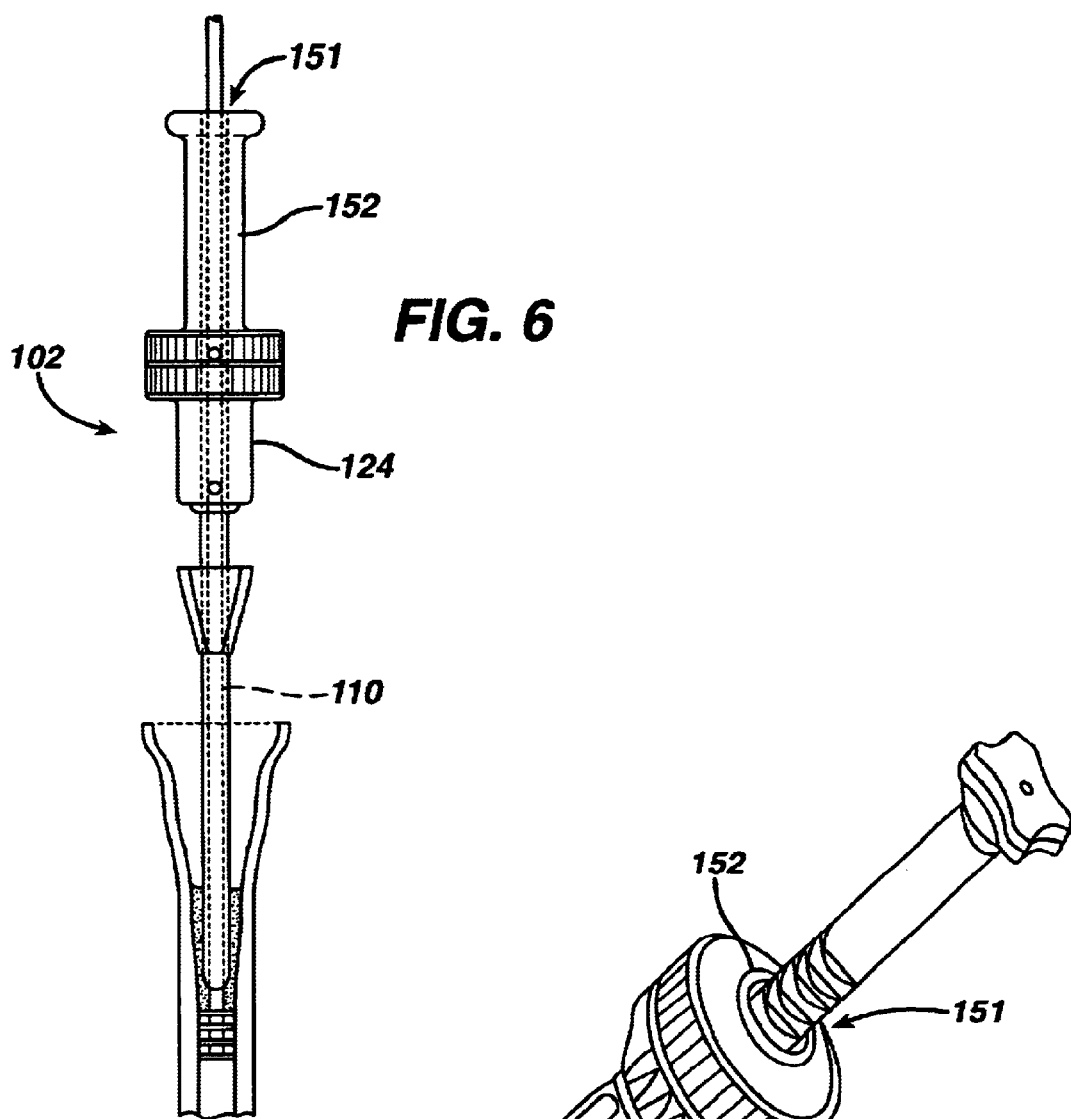
FIG. 6 is a side elevation, partially in section, through the assembly of another embodiment of the present invention showing an adapter sleeve.
Figure 7:
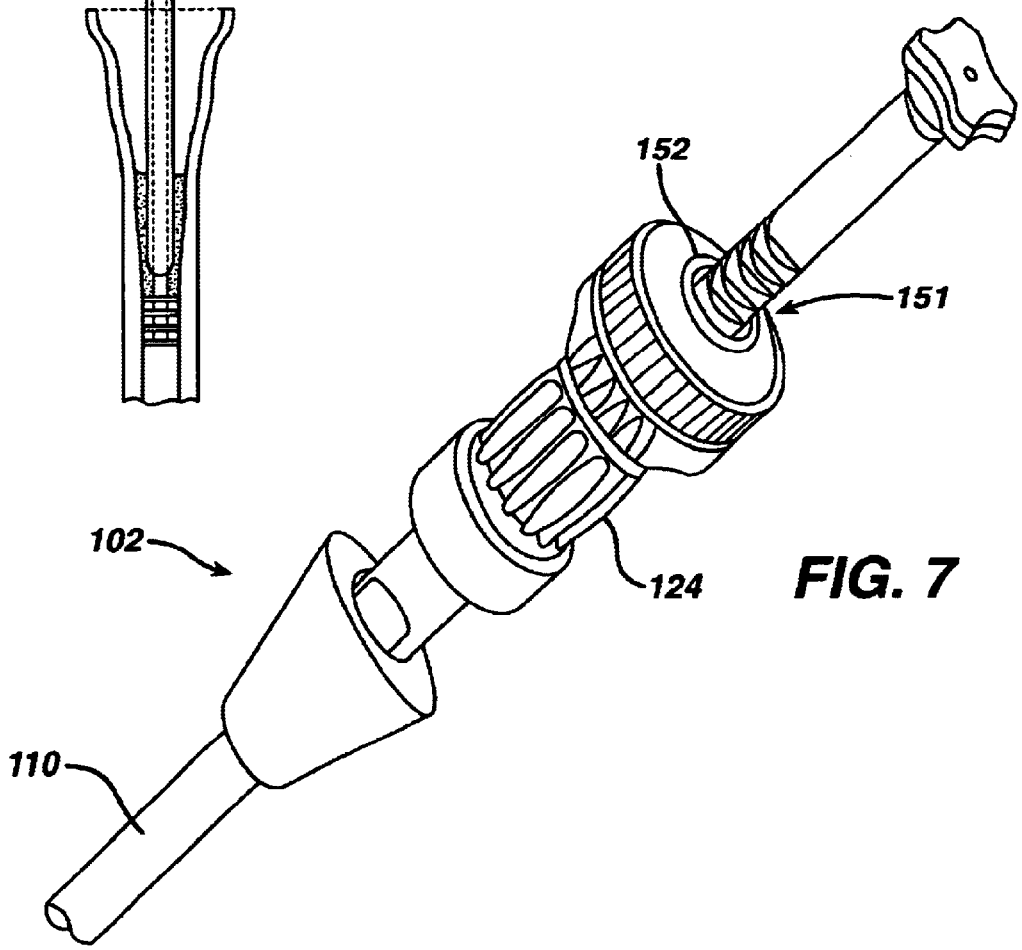
FIG. 7 is an isometric view of the hammer, proximal tamp portion and the proximal end of the distal tamp portion (which provides the guide shaft) of the tamp assembly shown in FIG. 6.

Referring now to FIGS. 6 and 7, the tamp assembly 102 is shown which includes a guide shaft 110 and a hammer 124 defining a bore 151 therewithin. The tamp assembly 102 includes an adaptor sleeve 152 which fits over the guide shaft 110 and within the bore 151.

Referring now to FIGS. 8 and 9, the tamp assembly 202 has a guide shaft 210 and a hammer 224. The hammer 224 slidably fits over the guide shaft 210. A distal tamp portion 254 is secured to the guide shaft 210. The distal tamp portion 254 and the guide shaft 210 can be separated.

The configuration of the cavity-end tamp portion will depend on the application for the assembly and will generally be selected to correspond to the shape of the resected end of the bone, which might be, for example, the tibia or the femur in the case of a knee joint prosthesis, or the femur in the case of a hip joint prosthesis.

In use, a cavity within a resected bone is first prepared to receive an implant, for example using a reamer. The nature of the preparation will depend on the technique by which the implant is to be fixed into the bone cavity. It will also depend on the condition of the bone and the dimensions of the selected implant.

A bone plug can be located in the bone cavity to restrict the depth to which filler material can be pushed into the cavity. The bone plug can have a threaded bore formed in it to receive a guide rod. These features are shown in FIG. 1.

A distal tamp portion is located in the bone cavity, with its tip located at an appropriate depth to define a cavity which will accommodate the selected implant. If the assembly is used with a guide rod extending from the bone plug, the distal tamp portion will be cannulated so as to be able to accommodate the guide rod. Filler material such as morcellised bone graft material is provided in the cavity, in the space between the distal tamp portion and the bone cavity wall.

A proximal tamp portion is selected which will compact a thin layer of morcellised bone graft between it and the bone cavity wall, in the region of the cavity towards the resected end of the bone in which the cross-section of the cavity begins to increase in size. It is connected to the hammer and the connected components are slid onto the distal tamp portion at its free upper end. Filler material within the cavity is then compressed by moving the hammer and proximal tamp portion along the guide shaft provided by the distal tamp portion, using a repeated up and down action. The cap on the guide shaft prevents the hammer from being moved so far along the guide shaft that it comes off.

Once filler material has been sufficiently compressed, the hammer and proximal tamp portion are removed from the guide shaft (after removing the cap if fitted). The tamp portion and is then separated from the hammer and replaced by another one which can be used to compress a thicker layer of filler material.

This process is repeated until the filler material fills the cavity within the bone to define a space within the cavity which has an appropriate configuration to receive the selected implant.

The hammer is then separated from the proximal tamp portion and is connected to a cavity-end tamp portion with an appropriate adaptor, which are used to finish the top surface of the filler material.

The tamp assembly, with any guide rod, is then removed from the bone cavity. The filler material that surrounds the distal tamp portion is only disturbed minimally when the distal tamp portion is removed. The disturbance that is suffers is less than would be the case if the distal tamp portion had been raised and lowered repeatedly, together with the proximal tamp portion and hammer.

What is claimed is:

1. A tamp assembly for use in configuring bone cavity filler material within a bone cavity, in preparation for receiving an implant, which comprises:
   - a distal tamp portion which has a substantially constant cross-section over at least part of its length,
   - a proximal tamp portion which has a through bore extending through it with a size which is such that the proximal tamp portion is a sliding fit over the distal tamp portion, and which has an exterior tamping surface extending from the through bore which faces generally towards the distal tamp portion,
   - a hammer for transmitting impact to the bone cavity filler material which is contacted by the exterior tamping surface of the proximal tamp portion, and
   - a cavity-end tamp portion having a through bore extending through it, whose size which is such that the cavity-end tamp portion is a sliding fit over the distal tamp portion, and which has a mould surface facing into the bone cavity when the cavity-end tamp portion is in use, to shape the bone cavity filler material to receive an implant at the exposed end of the cavity.

2. An assembly as claimed in claim 1, in which the proximal tamp portion and the hammer have mating formations which enable them to be fastened to one another.

3. An assembly as claimed in claim 1, in which the proximal tamp portion has an external cross-section at its distal end which corresponds approximately to the external cross-section of the distal tamp portion, and in which the tamping surface of the proximal tamp portion which faces towards the distal tamp portion is tapered outwardly from its distal end towards its proximal end.

4. An assembly as claimed in claim 1, in which the tamping surface of the proximal tamp portion which faces towards the distal tamp portion is generally planar.

5. An assembly as claimed in claim 1, which includes a plurality of distal tamp portions with a range of sizes, and a plurality of proximal tamp portions whose through bores have sizes which are such that each proximal tamp portion is a sliding fit on a corresponding one of the distal tamp portions.

6. An assembly as claimed in claim 1, which includes a plurality of proximal tamp portions whose through bores are substantially the same size so that all of the proximal tamp portions are a sliding fit over the distal tamp portion, the proximal tamp portions being tapered outwardly from the distal ends thereof towards their proximal ends, and differing in the configuration of the outward taper.

7. An assembly as claimed in claim 1, in which the distal end of the distal tamp portion is rounded.

8. An assembly as claimed in claim 1, in which the distal tamp portion and the guide shaft are formed as a single component.

9. An assembly as claimed in claim 8, which includes an adaptor sleeve which fits over the guide shaft and within the through bore within the hammer, to provide a sliding fit between the guide shaft and the hammer.

10. An assembly as claimed in claim 1, in which the distal tamp portion and the guide shaft can be separated.

11. A tamp assembly for use in configuring bone cavity filler material within a bone cavity, in preparation for receiving an implant, which comprises:
   - a distal tamp portion which has a substantially constant cross-section over at least part of its length,
   - a proximal tamp portion which has a through bore extending through it with a size which is such that the proximal tamp portion is a sliding fit over the distal tamp portion, and which has an exterior tamping surface extending from the through bore which faces generally towards the distal tamp portion, and
   - a hammer for transmitting impact to the bone cavity filler material which is contacted by the exterior tamping surface of the proximal tamp portion,
   - a guide shaft which is aligned with the distal tamp portion, the hammer having a through bore extending through it with a size which is such that it is a sliding fit over the guide shaft, and
   - a cap on the guide shaft with a impact surface facing along the guide shaft towards the proximal tamp portion, onto which impact can be directed to loosen the assembly from within the bone cavity.

12. An assembly as claimed in claim 11, in which the cap is arranged so that the impact surface so that it is engaged by the hammer as it is slid over the guide shaft.

* * * * *